US 8,170,642 B2

(12) United States Patent
Yan et al.

(10) Patent No.: US 8,170,642 B2
(45) Date of Patent: May 1, 2012

(54) METHOD AND SYSTEM FOR LYMPH NODE DETECTION USING MULTIPLE MR SEQUENCES

(75) Inventors: Michelle Xiao-Hong Yan, Princeton, NJ (US); Yue Lu, Chavannes-pres-Renens (CH); Martin Requardt, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1150 days.

(21) Appl. No.: 11/970,875

(22) Filed: Jan. 8, 2008

(65) Prior Publication Data
US 2008/0171932 A1      Jul. 17, 2008

Related U.S. Application Data

(60) Provisional application No. 60/884,512, filed on Jan. 11, 2007.

(51) Int. Cl.
*A61B 5/05* (2006.01)
*G06K 9/00* (2006.01)

(52) U.S. Cl. .................................. 600/410; 382/128
(58) Field of Classification Search .............. 382/128, 382/131, 132; 600/407, 410
See application file for complete search history.

(56) References Cited

U.S. PATENT DOCUMENTS

| 6,458,336 | B1 | 10/2002 | El-Tamer et al. | |
| 6,510,335 | B1 | 1/2003 | Miyazki | |
| 6,818,203 | B2 | 11/2004 | Platzek et al. | |
| 7,198,775 | B2 | 4/2007 | El-Tamer et al. | |
| 2005/0171424 | A1* | 8/2005 | Brechbiel et al. | 600/420 |
| 2007/0123773 | A1* | 5/2007 | Fuchs et al. | 600/410 |
| 2007/0286808 | A1 | 12/2007 | Bengi | |

OTHER PUBLICATIONS

J. Barentsz, "MR Imaging of Pelvic Lymph Nodes", Cancer Imaging 3:130-134,Dec. 2003.
D. Comaniciu, et al., "Mean Shift: A Robust Approach Toward Feature SpaceAnalysis", IEEE Trans. on Pattern Analysis & Machine Intelligence, 24(5):603-619, May 2002.
J. Dornheim, et al., "Segmentation of Neck Lymph Nodes in CT Datasets with Stable 3D Mass-Spring Models", Proc. of Medical Image Comp & Computer-Assisted Intervention, 2006.
M.G. Harisinghani, et al., "Sensitive, Noninvasive Detection of Lymph Node Metastases", PLoS Medicine, 1(3), Dec. 2004.
K. Kanazawa, et al., "Computer-Aided Diagnosis for Pulomonary Nodules Based on Helical CT Images", Med. Imag. Graph., 22(2):157-167, 1998.
Y. Lee, et al., "Automated Detection of Pulmonary Nodules in Helical CT Images Based on an Improved Template-Matching Technique", Trans. on Med. Imag., 20(7):595-604, 2001.
T. Okumura, et al., "Variable N-Quoit Filter Applied for Automatic Detection of Lung Cancer by X-Ray CT", Proc. CAR98 Tokyo, Japan, 242-247, 1998.
J. Yan, et al., "Lymph Node Segmentation from CT Images Using Fast Marching Method", Computerized Medical Imaging and Graphics, 28:33-38, 2004.

\* cited by examiner

*Primary Examiner* — Irakli Kiknadze

(57) ABSTRACT

A method and system for detecting lymph nodes in multiple complementary magnetic resonance (MR) sequences is disclosed. Anatomical landmarks, such as blood vessels, are extracted in a first MR sequence, such as an MR angiography (MRA) image. A search area is defined in at least one second MR sequence, such as a T1 weighted VIBE image, based on the anatomical landmarks extracted the first MR sequence. Lymph nodes are then detected in the search area of the second MR sequence. The lymph nodes can be detected by segmenting the search area into homogenous regions and determining whether each region is a lymph node using feature analysis.

24 Claims, 7 Drawing Sheets

102

104

METHOD AND SYSTEM FOR LYMPH NODE DETECTION USING MULTIPLE MR SEQUENCES

This application claims the benefit of U.S. Provisional Application No. 60/884,512, filed Jan. 11, 2007, the disclosure of which is herein incorporated by reference.

BACKGROUND OF THE INVENTION

The present invention relates to lymph node detection in magnetic resonance (MR) sequences, and more particularly, to automated lymph node detection using multiple MR sequences.

Humans have approximately 500-600 lymph nodes, which are important components of the lymphatic system. Lymph nodes act as filters to collect and destroy cancer cells, bacteria, and viruses. Radiologists examine the lymphatic system for cancer staging (i.e., diagnosing the extent or severity of a patient's cancer) and evaluation of patient progress in response to treatment. Accordingly, accurate localization and staging of metastatic lymph nodes are essential to the early detection and appropriate treatment of cancer.

Compared with the traditional procedure of lymph node dissection, non-invasive MR imaging based diagnosis and staging methods have far less complications and side effects, and can avoid unnecessary surgery. However, a single MR sequence may lack sufficient diagnostic information for lymph node localization. Accurate diagnosis may require multiple complementary MR sequences, which makes manual detection of lymph nodes vary labor intensive and tedious. Small lymph nodes are often missed in manual detection, even by highly-trained radiologists. Accordingly, computer assistance is desirable to assist with lymph node detection.

BRIEF SUMMARY OF THE INVENTION

The present invention addresses automated detection of lymph nodes. Embodiments of the present invention are directed to automatically detecting lymph nodes using multiple complementary magnetic resonance (MR) sequences of the same patient.

In one embodiment of the present invention, anatomical landmarks, such as blood vessels, are extracted in a first MR sequence, such as an MR angiography (MRA) image. The anatomical landmarks can be extracted in the first MR sequence using adaptive thresholding and a connect component analysis. A search area is then defined in at least one second MR sequence, such as a T1 weighted VIBE image and/or a T2* MEDIC image, based on the anatomical landmarks extracted in the first MR sequence. The search area can be defined by mapping the anatomical landmarks extracted in the first MR sequence to the second MR sequence and dilating the area defined by the anatomical landmarks in the second MR sequence to define the search area. Lymph nodes are then detected in the search area of the second MR sequence. The lymph nodes can be detected by segmenting the search area into homogenous regions and determining whether each region is a lymph node using feature analysis. The search area can be segmented using mean-shift clustering followed by region merging.

These and other advantages of the invention will be apparent to those of ordinary skill in the art by reference to the following detailed description and the accompanying drawings.

DETAILED DESCRIPTION

The present invention is directed to a method for lymph node detection in magnetic resonance (MR) sequences. An MR sequence, or volume, is made up of a sequence of 2D MR images or slices. Embodiments of the present invention are described herein to give a visual understanding of the lymph node detection method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
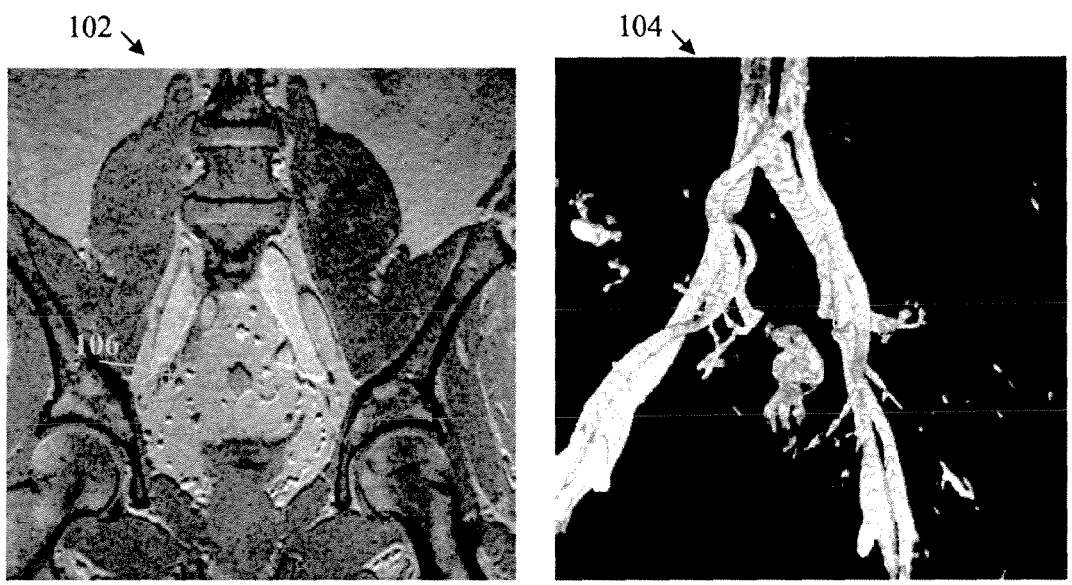
FIG. 1 illustrates exemplary T1-vibe and MRA images.

Embodiments of the present invention are directed to detecting lymph nodes using multiple complementary MR sequences. As defined herein, complementary MR sequences are different types of MR sequences of the same patient. It is well known that different type of MR sequences can be obtained using different MR scanning protocols. According to an embodiment of the present invention, pelvic lymph nodes can be detected using a 3D MR angiography (MRA) image and a high resolution 3D T1-weighted VIBE (T1-vibe) MR image of the same patient. In particular, embodiments of the present invention utilize an MRA image for landmark extraction and a T1-vibe image for 3D anatomy and shape analysis. MRA and T1-vibe images are well-known types of MR sequences. FIG. 1 illustrates exemplary T1-vibe and MRA images. Image 102 of FIG. 1 is a slice of a 3D T1-vibe image and image 104 of FIG. 1 is a 3D rendered view of an MRA image. As illustrated in FIG. 1, the T1-vibe image 102 has well defined boundaries between different types of soft tissues and can be used as an anatomic reference. For example, a lymph node 106 in the T1-vibe image 102 can appear as a dark-grey and/or isolated region, which is close to blood vessels. The MRA image 104 is generated using a contrast agent that increases the contrast of the blood vessels in the image, which makes it easier to find major blood vessel manually or automatically.

Although, embodiments described herein utilize MRA and T1-vibe MR images to detect pelvic lymph nodes, it is to be understood that the present invention is not limited thereto and other types of MR sequences can be used to detect lymph nodes in the pelvis and other parts of the body. For example, it is possible that an additional contrast enhanced MR image, such as a T2* MEDIC image can be used to improve detection and accuracy of malignant lymph nodes. Similarly, any other type of MR sequence can be used in addition to or in place of the described MR sequence types to detect lymph nodes.

Figure 2:
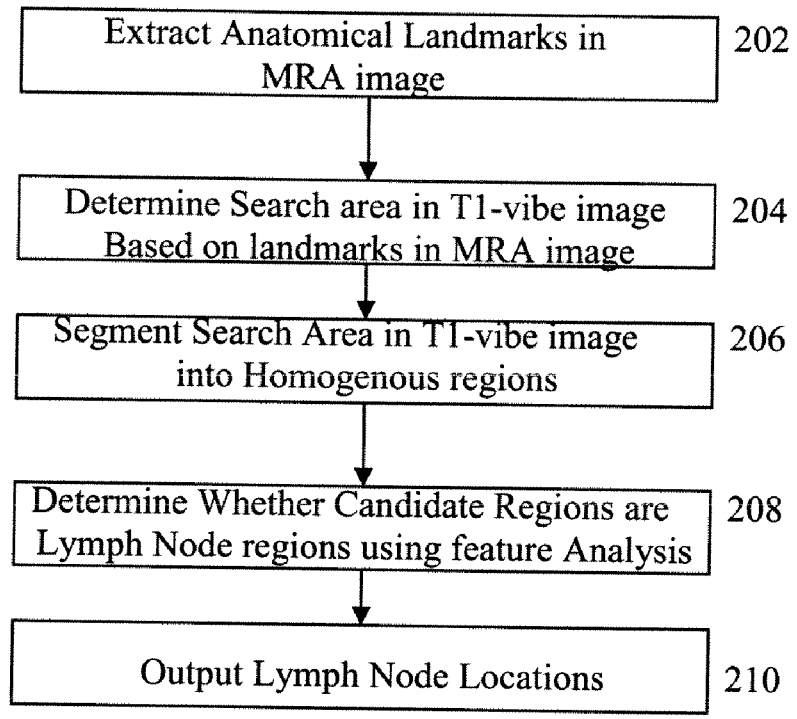
FIG. 2 illustrates a method for detecting lymph nodes using multiple complementary MR sequences according to an embodiment of the present invention.

FIG. 2 illustrates a method for detecting lymph nodes using multiple complementary MR sequences according to an embodiment of the present invention. The method of FIG. 2 utilizes an MRA image and a T1-vibe image as the complementary MR sequences. Accordingly, an MRA image and a T1-vibe image of the pelvic region are obtained of the same patient. These MR sequences can be obtained using well-known MR scanning techniques. It is also possible that previously scanned and stored MR image sequences can be input in order to detect lymph nodes in the MR sequences.

At step 202, anatomical landmarks are extracted in the MRA image. Pelvic Lymph nodes are typically present near blood vessels. Accordingly, blood vessels are an important anatomical landmark that can be used to guide the lymph node detection. Blood vessels can be extracted in the MRA image and used to define a 3D search area. The blood vessels can be extracted using adaptive thresholding followed by a connected component analysis.

In MRA imaging, a contrast agent is injected into the bloodstream. Accordingly, the blood vessels and organs perfused with the contrast agent appear substantially brighter in image intensity than surrounding tissues in an MRA image. In order to extract the vessel tree from the MRA image, adaptive thresholding is performed to isolate bright regions which possibly form the vessel tree. Any voxel in the MRA image whose intensity value is above a threshold $T_{vessel}$ is retained into the set $S_{T,MRA}$. The threshold $T_{vessel}$ can be globally selected to be the top 2% intensity value in the MRA image, i.e., $$\#\{I_i : I_i \geq T_{vessel}, i=0, \ldots, N\} = 0.02 \times N,$$

where $I_i$ is the intensity of the ith voxel and N is the total number of voxels in the MRA image. A connect component analysis (e.g., 26-connectivity) can then be applied to $S_{T,MRA}$, such that only the largest connected structure $S'_{MRA}$ is retained as the vessel tree. This removes small components which presumably arise from other structures (e.g., intestines) and image degradations.

At step 204, a search area is determined in the T1-vibe image based on the anatomical landmarks extracted in the MRA image. Since lymph nodes are typically found near major blood vessels, an area surrounding the vessel tree extracted from the MRA image can be defined as the search area. Accordingly, the search area can be determined in the T1-vibe image by mapping the vessel tree extracted in the MRA image to the T1-vibe image and expanding the vessel tree to define the search area. Depending on the degree of motion present between the complementary MR sequences, rigid and/or non-rigid registrations may be necessary in order to apply the locations of the vessels to the T1-vibe image. Registration may not be necessary if the MRA image and the T1 image are obtained at or near the same time as each other with little or no patient movement. Since the blood vessel tree is expanded to define the search area, a perfect registration may not be needed.

In one implementation of the present invention, the vessels $S'_{MRA}$ extracted in the MRA image are mapped to corresponding locations $S'_{T1}$ in the T1-vibe image using a linear transformation:

$$x_2 = \Lambda_2^{-1} R_2^{-1} (R_1 \Lambda_1 x_1 + (T_1 - T_2)),$$

where $x_i$, $\Lambda_i$, $R_i$, $T_i$ (for i=1, 2) are the volume coordinates, scaling matrices, rotation matrices, and translation matrices of the two sequences (MRA and T1-vibe), respectively. The parameters in the transformation matrices can be obtained in the image description files associated with the MRA and T1-vibe images. After the linear mapping, the vessel area $S'_{T1}$ can be dilated with a predetermined radius in order to form the search area $S_{T1}^{Search}$. For all subsequent method steps for detecting lymph nodes, only the voxels inside the search area $S_{T1}^{Search}$ are considered.

Figure 3:
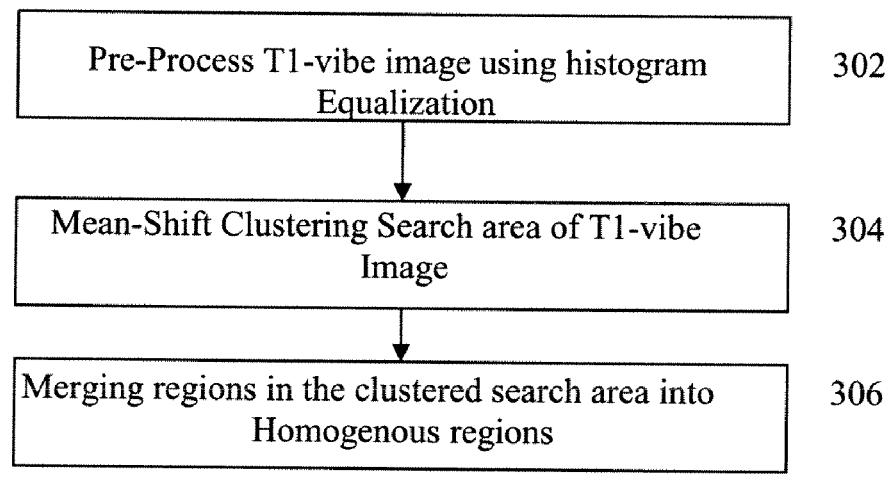
FIG. 3 illustrates a method of segmenting a search area into homogenous regions according to an embodiment of the present invention.

At step 206, the search area in the T1-vibe image is segmented into homogenous regions. A 3D mean-shift clustering method can be used to segment the search area of the T1-vibe image into a multiple homogenous regions. This step filters out unwanted patterns, including noise and other irrelevant small or large structures, while retaining significant anatomical structures and lymph nodes. FIG. 3 illustrates a method of segmenting the search area into homogenous regions according to an embodiment of the present invention. Accordingly, the steps of FIG. 3 can be used to implement step 206 of FIG. 2.

Referring to FIG. 3, at step 302, the T1-vibe image is pre-processed using histogram equalization within the search area. Even when targeted at the same body parts, the intensity distribution of T1-vibe images can vary from case to case. In order to make the lymph node detection less sensitive to such variations, the T1-vibe image can be pre-processed using histogram equalization. A histogram of the intensities of T1-vibe image within the search area can be converted into a standard histogram through a non-linear mapping:

$$L(I) = \operatorname*{argmax}_J \left\{ \sum_{j=1}^{J} H_0(j) \leq \sum_{i=1}^{I} H(i) \right\},$$

where $H_0$ and H are the normalized histograms of the standard and current images, respectively.

At step 304, 3D mean-shift clustering is performed in the search area. Mean-shift clustering is a powerful tool for density estimation and discontinuity preserving smoothing, which filters out unwanted patterns, including noise and other irrelevant small structures, while retaining significant anatomical structures and lymph nodes in the search area. In the mean-shift clustering method, each voxel in the search area of the T1-vibe image is considered to be a point $$p_i = \left( \frac{x_i}{S}, \frac{y_i}{S}, \frac{z_i}{S}, \frac{I_i}{R} \right)$$

in the 4-dimensional feature space, with the first three elements being its spatial location, and the last element being its intensity (range) value. To accommodate the different natures of these features, they are normalized by the spatial bandwidth parameter S and the range bandwidth parameter R, respectively. The entire search area of the T1-vibe image forms a point cloud in the 4-D domain. The mean-shift clustering algorithm iteratively attempts to find locations where the density of the point cloud reaches a local maximum (i.e., modes). The means-shift clustering algorithm used to segment the search area of the T1-image is described as follows.

Let $X_i$, i=1, ..., N, be the input feature in the normalized 4-D domain. For each voxel i in the search area, the initial iteration is initialized so that voxel is equal to the input feature for that voxel, i.e., n=1, $p_{i,1}=x_i$. The following expression is then repeated iteratively for each voxel i:

$$p_{i,n} = \frac{1}{N}\sum_{j=1}^{N} \phi(p_{j,n-1}, p_{i,n-1}) \cdot p_{j,n-1}, \quad (1)$$

where $p_{i,n-1}$ and $p_{i,n}$ are the iteration results at the (n−1)th and nth steps, respectively, and $\phi(\cdot,\cdot)$ is the clustering kernel. A simple uniform clustering kernel can be selected, such that the clustering kernel is defined as:

$$\phi(p_i, p_j) = \begin{cases} 1, & \text{if } \|p_i^S - p_j^S\| \le 1 \text{ and } \|p_i^R - p_j^R\| \le 1 \\ 0, & \text{otherwise.} \end{cases}$$

where $p_i^S$ is the 3D spatial feature and $p_i^R$ is the 1-D range feature. Thus, in (1), the sum is carried on a small subspace.

The iteration expressed in (1) is repeated until either the means shift vector $\|p_{i,n}-p_{i,n-1}\|$ is small enough, or $\|p_{i,n}^R - x_{p_i^s}^{R^{in}}\| \le 1$. Here, $x_{p_i^s}^R$ refers to the input range feature at the spatial location of $p_{i,n}^S$. Upon convergence for each i, the converged range feature is assigned to the output, $z_i=(x_i^S, p_{i,c}^R)$. This algorithm defines a region or class for each voxel by assigning the mean intensity value of a unit sphere centered at each voxel to that voxel. The iteration expressed in (1) is guaranteed to converge.

At step 306, clustered regions in the search area of the T1-vibe image are merged into homogenous regions. The mean-shift clustering of step 304 can result in an over-segmented image. Accordingly, a graph-theoretic region merging method (transitive closure) can be applied to the mean-shift clustered search area of the T1-vibe image to merge regions in the clustered search area into multiple homogenous regions. The graph-theoretic region merging method can include steps of initialization, region adjacency graphing, merging, and pruning.

In the initialization step of the graph-theoretic region merging method, the graph-theoretic region merging method can use a connect component analysis to delineate the clusters in the mean-shifted intensities $\{I_i\}_{i=1,\ldots,N}$. Voxels i and j are considered to belong to the same cluster if they are neighbors (e.g., by 26-connectivity) and $\|I_i-I_j\|\le 1$. The clusters $\{C_k\}_{k=1,\ldots,M}$ formulate the initial regions.

In the region adjacency graphing step of the graph-theoretic region merging method, a graph can be generated by a raster scan of the clustered search area of the T1-vibe image in order to identify the neighboring relations between regions (nodes). Every node in the graph represents a segmented region, and two nodes are connected only if the two corresponding regions are connected in the spatial domain. The mean intensity $\{C_k\}_{k=1,\ldots,M}$ and size $\{N_k\}_{k=1,\ldots,M}$ of each regions are then stores in the corresponding node.

In the merging step of the graph-theoretic region merging method, for each node k, the neighboring nodes are checked, and the node k is merged with those nodes j satisfying $\|C_k - C_j\| \le T_{merge}$, where $T_{merge}$ is an intensity threshold for region merging. This process is repeated until no more regions are merged. At each iteration, the graph is reconstructed to reflect the changes in the neighborhood relationship, as well as the region size and mean intensity.

In the pruning step of the graph-theoretic region merging method, for each node k, if the size of the region satisfies $\{N_k\}\le T_{prune}$, then the node k is merged with a neighboring node j that minimizes $\|C_k-C_j\|$. Here, $T_{prune}$ is a size threshold for pruning. Accordingly, regions smaller than a certain size are merged with the most similar neighboring region. This process is repeated until no small regions remain, and the graph is updated iteratively.

The graph-theoretic region merging method takes into account both spatial and intensity relationships of two regions. Ideally, the image merging could be carried out on the 3D T1-vibe MR volume. However, due to the fact that many lymph nodes are spatially attached to, and have similar intensities as, other large structures, (e.g., vessels, muscles), such lymph nodes would be "ruled out" after the 3D merging process. Also, the calculation of the 3D regional graph for a typical volume may be time-consuming. A 3D-2D-3D procedure can be used, as described herein.

From a 3D volume of the mean-shifted T1-vibe image, 2D slices can be generated in three different views: coronal, sagittal, and transverse. For each slice in a certain view, 2D region merging can be applied to segment different homogenous regions. In each region, the statistic features include size and mean intensity. By fitting an ellipse to the region using Principal Component Analysis (PCA), shape features can be calculated, including the ratio of the long axis to the short axis, the algebraic distance, and the occupancy (the ratio of region size to ellipse size). From these features, constraints can be formulated based on prior knowledge of lymph nodes. Only a small set of 2D regions that satisfy the constraints are retained for further analysis. The 2D candidate regions from 3 different views are merged together into a 3D volume. A 2D region from view i can be merged with another region from view j, if they have at least one voxel in common. Those regions that do not have connected regions from other views can be removed, since intuitively a lymph node region should be detected in at least two views. The remaining 3D homogenous regions are candidate regions to be lymph nodes.

The purpose of the 2D region analysis is to increase the detection rate (i.e., sensitivity) of the lymph nodes. The region merging process highly depends on the parameter of merging criteria ($T_{merge}$), and may not be robust. This can be improved by repeating the process for multi-slices and multi-views. A candidate region can remain for further analysis if one of its 2D slices in at least 2 views is correctly segmented. On the other hand, a majority of the 2D regions are eliminated based on the 2D feature test, which can increase the specificity rate (i.e., the ratio of true positives to all of the candidate regions).

Returning to FIG. 2, at step 208 it is determined whether the candidate regions are lymph nodes using feature analysis. In order to determine whether each candidate region in the search area is a lymph node, a linear classifier can be trained based on multiple lymph node features. The linear classifier is applied to the candidate regions to analyze each candidate region based on features of the candidate region such as, local contrast, 3D shape, and relative location to other anatomical structures. The linear classifier can determine for each candidate region how likely it is that the candidate region is a lymph node. Examples of features that can be used in this feature analysis are described as follows.

One such feature is the mean and variance of the intensity of the candidate region. The mean and variance of the intensity is the average and standard deviation of intensity for all voxels within the 3D candidate region. This feature reduces false positives which may appear due to stools and vessels having similar shapes to lymph nodes. Another possible feature is the volume and centroid location, which can be determined for a candidate region as the total number of voxels in the region and the coordinates of the centroid of the region, respectively. Another possible feature is the long axis, medium axis, short axis, and aspect ratio for a candidate region. The three axes can be calculated after using PCA to fit an ellipsoid to the 3D candidate region. The ratio between the long axis and the medium axis, as well as the ratio between the long axis and the short axis can then be calculated. The aspect ratio between the long axis and the short axis is an important indicator of the shape of the candidate region, since lymph nodes tend to have aspect ratios close to 1, while elongated structures such as vessels have larger aspect ratios. Another possible feature is the 3D occupancy of a candidate region. The 3D occupancy of a candidate region is the volume of the 3D candidate region versus the volume of the corresponding ellipsoid. This feature indicates the fitness of the ellipsoid to the candidate region. Another possible feature is the highest, medium, and lowest 2D occupancy ratio for a candidate region at three different views (coronal, sagittal, and transversal). These features can indicate the best or worst node-like 2D slice in the candidate region, and help to identify a node that is only correctly segmented in one or two slices. Another possible feature is the number of 2D slices that the 3D candidate region contains. It is to be understood that the features described herein are exemplary, and other features can be used as well.

Figure 4:
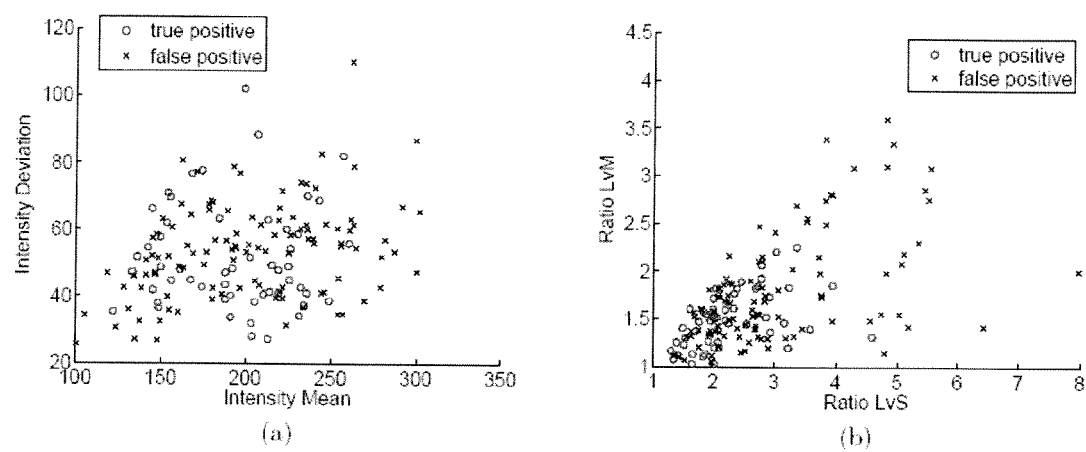
FIG. 4 illustrates exemplary feature distributions of true positives and false positives for detected lymph nodes.

Once the feature analysis is used to determine whether each candidate region is a lymph node, the regions determined as lymph nodes can be pruned to reduce false positives. The lymph node regions can be pruned based on features which are typically different for true positives and false positives. FIG. 4 illustrates exemplary feature distributions of true positives and false positives. As illustrated in FIG. 4, graph (a) shows a distribution of intensity mean versus intensity standard deviation for true positives and false positives, and graph (b) shows a distribution of the ratio of long axis versus short axis (LvS) versus the ratio of long axis versus medium axis (LvM) for true positives and false positives. According to the features shown in FIG. 4, elimination conditions to eliminate false positives can be formulated as:

$Ratio_{LvS}>4.0;$ $Ratio_{LvM}>2.6;$ $Ratio_{LvS}>3.0$ and $Ratio_{LvM}>1.8;$ $Mean_{Intensity}>130$, and either $Variance_{Intensity}>42.5$ or $Variance_{Intensity}<37.5.$ Thus, in order to reduce false positives, a candidate region can be eliminated if the candidate region satisfies any of the elimination conditions listed above. It is to be understood that the elimination conditions described above are exemplary, and other eliminations can be defined similarly for other features. For example, the distance from candidate regions to blood vessels is another feature that can be used to prune the candidate regions.

Figure 5:
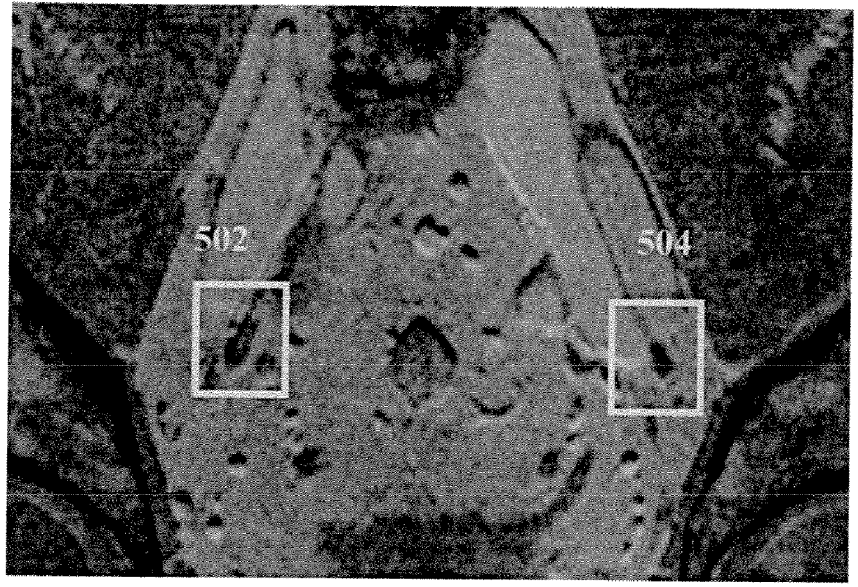
FIG. 5 illustrates exemplary T1-vibe and T2* MEDIC images.
Figure 5:
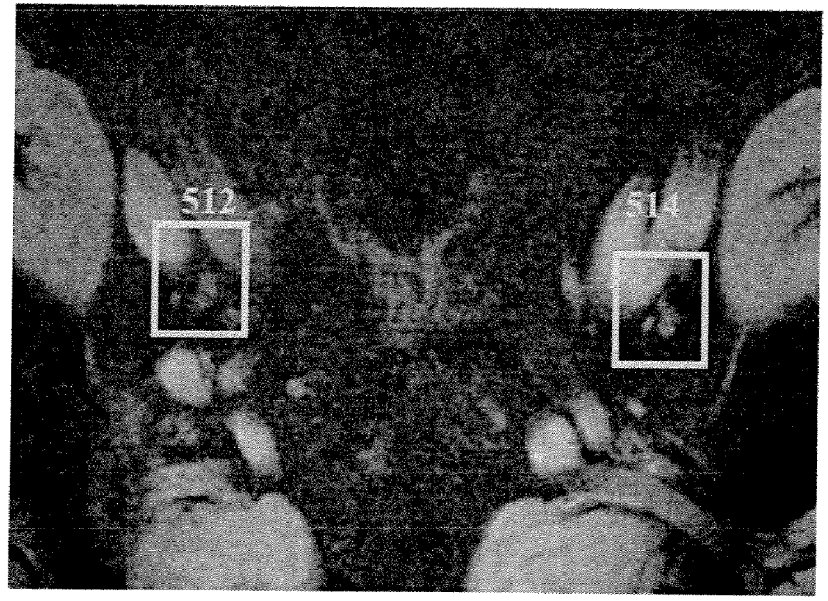

As described above, the method of FIG. 2 utilizes an MRA image and a T1-vibe image for lymph node detection, but the present invention is not limited thereto. According to another embodiment of the present invention, another MR image sequence can be used together with the T1-vibe image for the segmentation and feature analysis steps of FIG. 2. For example, a T2* MEDIC image can be used together with the T1-vibe image for segmentation and feature analysis in the search area determined based on the anatomical features detected in the MRA image. A T2* MEDIC image is a contrast enhanced MR sequence in which the contrast of malignant lymph nodes is increased. Accordingly, information from the T2* MEDIC image can be used in the feature analysis to detect malignant lymph nodes. FIG. 5 illustrates exemplarily T1-vibe and T2* MEDIC images. As illustrated in FIG. 5, image 500 is a slice of T1-vibe image in which regions 502 and 504 show malignant lymph nodes. Image 510 is a complementary slice of a T2* MEDIC image. As shown in image 510, the contrast is enhanced in regions 512 and 514, which correspond to regions 502 and 504 of image 500, making malignant lymph nodes easier to detect using the T2* MEDIC image.

Figure 6:
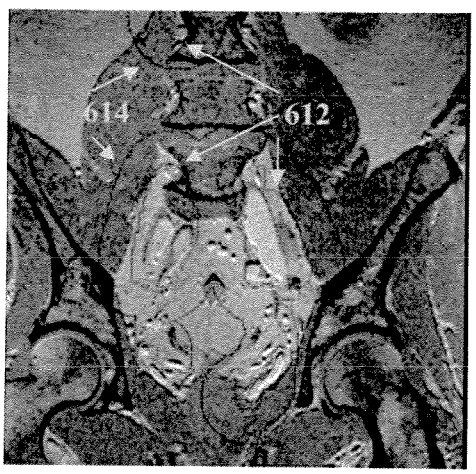
FIG. 6 illustrates exemplary results of lymph node detection using the method of FIG. 2.
Figure 6:
Figure 6:
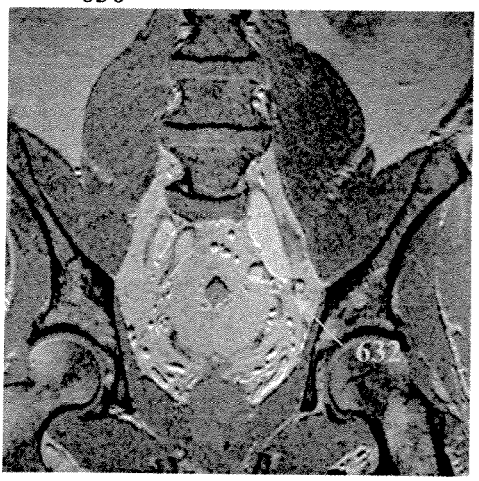
Figure 6:
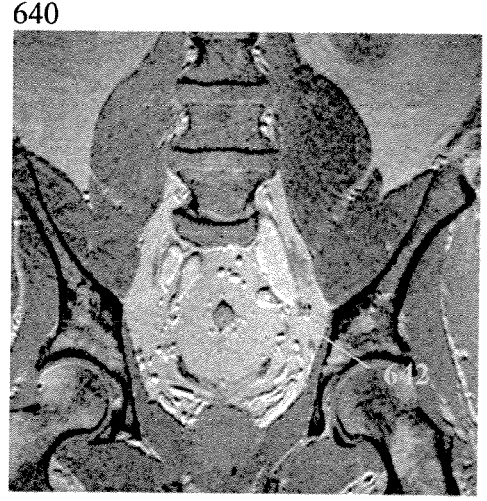

FIG. 6 illustrates exemplary results of lymph node detection using the method of FIG. 2. As illustrated in FIG. 6, image 610 shows a vessel tree 612, which was extracted from an MRA image, applied to a T1-vibe image. A search area 614 in the T1-vibe image is determined by dilating the extracted vessel tree 612 with a pre-determined radius. For all subsequent method steps, such as segmentation and feature analysis, only voxels within the search area 614 are considered. Image 620 shows the T1-vibe image after mean-shift clustering. As shown in image 620, the mean-shift clustering results in a more homogenous image. Image 630 shows a lymph node 632 detected in the T1-vibe image after region merging and feature analysis. Image 640 shows a manually labeled lymph node 642 in the T1-vibe image. Comparing the lymph node 632 in image 630 detected automatically using an embodiment of the present invention with the lymph node 642 in image 640 detected manually, it can be seen that the present invention detects the lymph node accurately.

Figure 7:
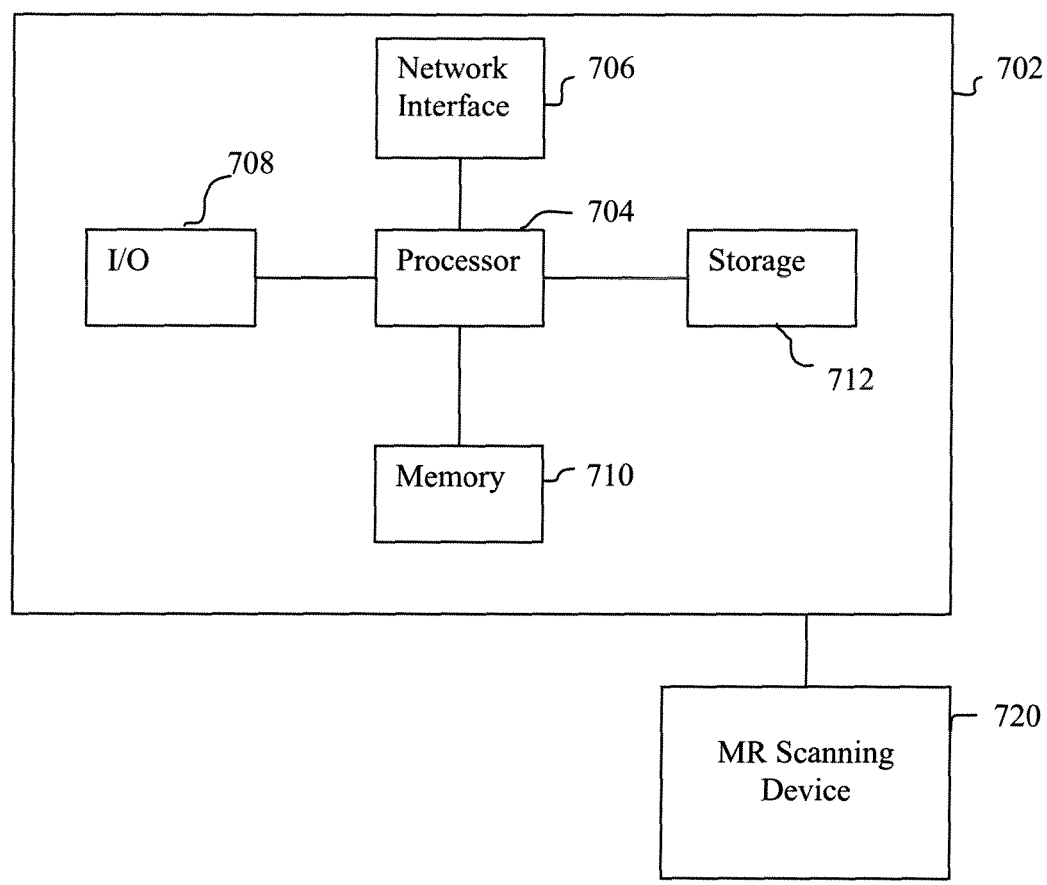
FIG. 7 is a high level block diagram of a computer capable of implementing the present invention.

The above-described methods for lymph node detection may be implemented on a computer using well-known computer processors, memory units, storage devices, computer software, and other components. A high level block diagram of such a computer is illustrated in FIG. 7. Computer 702 contains a processor 704 which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the method of FIGS. 2 and 3 may be defined by the computer program instructions stored in the memory 710 and/or storage 712 and controlled by the processor 704 executing the computer program instructions. An MR scanning device 720 can be connected to the computer 702 to input the MR sequences to the computer 702. It is possible to implement the MR scanning device 720 and the computer 702 as one device. It is also possible that the MR scanning device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention.

Those skilled in the art could implement various other feature combinations without departing from the scope and spirit of the invention.

What is claimed is:

1. A method for detecting lymph nodes using multiple complementary magnetic resonance (MR) sequences, comprising:
    extracting anatomical landmarks in a first MR sequence;
    determining a search area in at least one second MR sequence based on the anatomical landmarks extracted in said first MR sequence; and
    detecting lymph nodes in said search area of said at least one second MR sequence.

2. The method of claim 1, wherein said step of detecting lymph nodes comprises:
    segmenting said search area of said at least one second MR sequence into multiple homogenous regions to determine candidate regions; and
    determining whether each of the candidate regions is a lymph node using feature analysis.

3. The method of claim 2, wherein said step of segmenting said search area of said at least one second MR sequence comprises:
    pre-processing said at least one second MR sequence using histogram equalization;
    mean-shift clustering said search area of said at least one second MR sequence into multiple homogenous regions; and
    merging homogenous regions in said search area based on intensity and size to determine said candidate regions.

4. The method of claim 3, wherein said step of mean-shift clustering said search area comprises:
    assigning to each of a plurality of voxels in said search area an intensity value equal to a mean intensity value of a unit sphere centered at that voxel.

5. The method of claim 3, wherein said step of merging homogenous regions in said search area comprises:
    generating a region adjacency graph in which each of the homogenous regions in said search area is represented by a corresponding node in the region adjacency graph;
    merging neighboring nodes when neighboring homogenous regions corresponding to the neighboring nodes have a similar intensity; and
    when a homogenous region has a size that is smaller than a threshold, merging the node corresponding to that homogenous region with a node corresponding to a neighboring homogeneous region having an intensity closest to an intensity of that homogenous region.

6. The method of claim 2, wherein said step of detecting lymph nodes further comprises:
    pruning candidate regions determined to be lymph nodes based on at least one of intensity, shape, and distance to blood vessels to eliminate false positives.

7. The method of claim 1, wherein said step of extracting anatomical landmarks in a first MR sequence comprises:
    segmenting anatomical landmarks in said first MR sequence using adaptive thresholding; and
    performing a connect component analysis on the segmented anatomical landmarks.

8. The method of claim 1, wherein said step of determining a search area in at least one second MR sequence comprises:
    mapping the anatomical landmarks extracted in said first MR sequence to said at least one second MR sequence; and
    dilating the anatomical landmarks in said at least one second MR sequence to define a search area in said at least one second MR sequence.

9. The method of claim 8, wherein said step of mapping the anatomical landmarks extracted in said first MR sequence to said at least one second MR sequence comprises:
    registering the anatomical landmarks to said at least one second MR sequence using a linear transformation.

10. The method of claim 1, wherein said step of extracting anatomical landmarks in a first MR sequence comprises:
    extracting a vessel tree in said first MR sequence.

11. The method of claim 1, wherein said first MR sequence comprises an MR angiography (MRA) image and said at least one second MR image comprises a T1 weighted VIBE image.

12. The method of claim 1, wherein said first MR sequence comprises an MR angiography (MRA) image and said at least one second MR image comprises a T1 weighted VIBE image and a T2* MEDIC image.

13. An apparatus for detecting lymph nodes using multiple complementary magnetic resonance (MR) sequences, comprising:
    means for extracting anatomical landmarks in a first MR sequence;
    means for determining a search area in at least one second MR sequence based on the anatomical landmarks extracted in said first MR sequence; and
    means for detecting lymph nodes in said search area of said at least one second MR sequence.

14. The apparatus of claim 13, wherein said means for detecting lymph nodes comprises:
    means for segmenting said search area of said at least one second MR sequence into multiple homogenous regions to determine candidate regions; and
    means for determining whether each of the candidate regions is a lymph node using feature analysis.

15. The apparatus of claim 14, wherein said means for segmenting said search area of said at least one second MR sequence comprises:
    means for pre-processing said at least one second MR sequence using histogram equalization;
    means for mean-shift clustering said search area of said at least one second MR sequence into multiple homogenous regions; and
    means for merging homogenous regions in said search area based on intensity and size to determine said candidate regions.

16. The apparatus of claim 14, wherein said means for detecting lymph nodes further comprises:
    means for pruning candidate regions determined to be lymph nodes based on at least one of intensity, shape, and distance to blood vessels to eliminate false positives.

17. The apparatus of claim 13, wherein said means for determining a search area in at least one second MR sequence comprises:
    means for mapping the anatomical landmarks extracted in said first MR sequence to said at least one second MR sequence; and
    means for dilating the anatomical landmarks in said at least one second MR sequence to define a search area in said at least one second MR sequence.

18. The apparatus of claim 13, wherein said first MR sequence comprises an MR angiography (MRA) image, said at least one second MR image comprises a T1 weighted VIBE image, and said anatomical landmarks are blood vessels.

19. A non-transitory computer readable medium encoded with computer executable instructions for detecting lymph nodes using multiple complementary magnetic resonance (MR) sequences, the computer executable instructions defining steps comprising:

extracting anatomical landmarks in a first MR sequence;

determining a search area in at least one second MR sequence based on the anatomical landmarks extracted in said first MR sequence; and detecting lymph nodes in said search area of said at least one second MR sequence.

20. The non-transitory computer readable medium of claim 19, wherein the computer executable instructions defining the step of detecting lymph nodes comprise computer executable instructions defining the steps of:

segmenting said search area of said at least one second MR sequence into multiple homogenous regions to determine candidate regions; and determining whether each of the candidate regions is a lymph node using feature analysis.

21. The non-transitory computer readable medium of claim 20, wherein the computer executable instructions defining the step of segmenting said search area of said at least one second MR sequence comprise computer executable instructions defining the steps of:

pre-processing said at least one second MR sequence using histogram equalization;

mean-shift clustering said search area of said at least one second MR sequence into multiple homogenous regions; and merging homogenous regions in said search area based on intensity and size to determine said candidate regions.

22. The non-transitory computer readable medium of claim 19, wherein the computer executable instructions defining the step of determining a search area in at least one second MR sequence comprise computer executable instructions defining the steps of:

mapping the anatomical landmarks extracted in said first MR sequence to said at least one second MR sequence; and dilating the anatomical landmarks in said at least one second MR sequence to define a search area in said at least one second MR sequence.

23. The non-transitory computer readable medium of claim 19, wherein the computer executable instructions defining the step of extracting anatomical landmarks in a first MR sequence comprise computer executable instructions defining the step of:

extracting a vessel tree in said first MR sequence.

24. The non-transitory computer readable medium of claim 19, wherein said first MR sequence comprises an MR angiography (MRA) image and said at least one second MR image comprises at least one of a T1 weighted VIBE image and a T2* MEDIC image.

* * * * *